United States Patent [19]

Menicacci

[11] Patent Number: 4,698,020
[45] Date of Patent: Oct. 6, 1987

[54] ATTACHMENT FOR A PARTIAL, REMOVABLE, DENTAL PROTHESIS

[76] Inventor: Ivano Menicacci, Via Goito 57, I-57100 Livorno, Italy

[21] Appl. No.: 806,279

[22] Filed: Dec. 6, 1985

[51] Int. Cl.⁴ .............................................. A61C 13/12
[52] U.S. Cl. .................................... 433/177; 433/181; 433/182
[58] Field of Search ............... 433/180, 181, 182, 183, 433/177, 178

[56] References Cited

U.S. PATENT DOCUMENTS

| | | | |
|---|---|---|---|
| 1,621,702 | 3/1927 | Yantis | 433/181 |
| 1,664,433 | 4/1928 | Seabrook | 433/182 |
| 1,863,230 | 6/1932 | Shapiro | 433/177 |
| 2,572,714 | 10/1951 | Funderburg | 433/177 |
| 2,705,366 | 4/1955 | Van Dyk | 433/182 |
| 3,117,377 | 1/1964 | Poreromo | 433/182 |

FOREIGN PATENT DOCUMENTS

| | | | |
|---|---|---|---|
| 868047 | 5/1953 | Fed. Rep. of Germany | 433/183 |
| 1202335 | 1/1960 | France | 433/177 |
| 640687 | 7/1950 | United Kingdom | 433/183 |

*Primary Examiner*—John J. Wilson
*Attorney, Agent, or Firm*—McGlew and Tuttle

[57] ABSTRACT

In order to activate, through a fine adjustment, the retention element (16) of an attachment for a partial, removable, dental prosthesis made up of two coulisses (1, 51), one of which being incorporated in the prosthesis (P) and the other (51) secured to a pillar tooth (D) there are utilized: a horizontal pivot (14) mounted in a sheath (2) and carrying, at one end, a retaining small head (16) and, at the other end, a bevel gear (5); and a cylindrical body (4') with vertical axis, mounted in a box (3) and carrying a bevel gear (4) which is in meshing engagement with the other hand gear (5). The base of the body (4') is provided with an operative groove (12) surfacing in the alveolar saddle (5) of the prosthesis (P). The rotation of the element (4') causes the displacement, along the pivot (14), of a plate (19) which compresses a counteracting spring (18) whose tensioning determines the retaining force of the attachment. The sheath (2) and the box (3) are held, in a removable way, in a container (1) associated with the coulisse incorporated in the prosthesis. The shape of the retention small head (16, 16', 16") in cooperation with the coulisse (51) secured to the pillar tooth, determines the working characteristics of, respectively, a rigid, semi-rigid, sprung, attachment.

10 Claims, 12 Drawing Figures

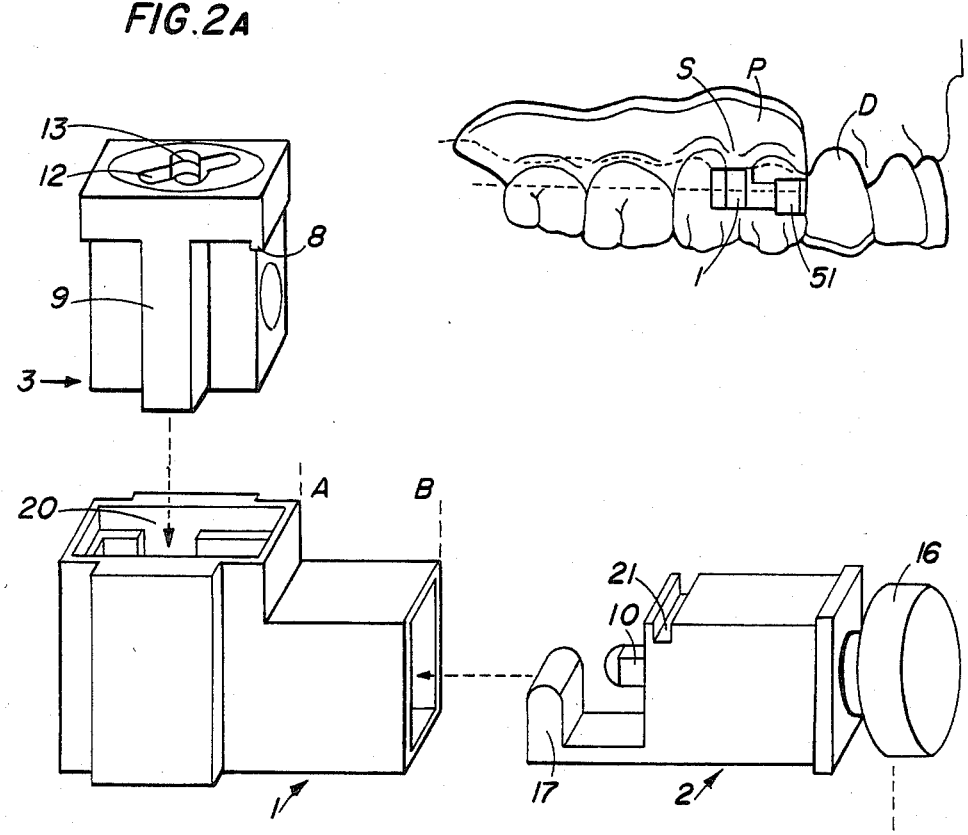
FIG. 1
FIG. 2A
FIG. 2B
FIG. 2C
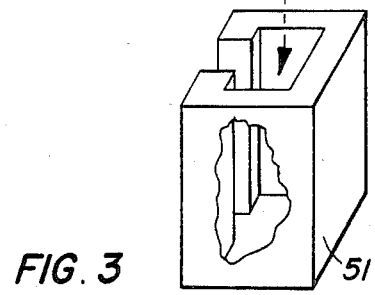
FIG. 3

ATTACHMENT FOR A PARTIAL, REMOVABLE, DENTAL PROTHESIS

FIELD AND BACKGROUND OF THE INVENTION

The present invention refers to an attachment for a partial, removable dental prosthesis.

It is known to use a partial removable prosthesis when the number and disposition of the remaining teeth of an arch do not admit the application of a fixed prosthesis or bridge. A removable prosthesis comprises a saddle resting on the maxillary bones and an anchorage to at least a pillar tooth by means of hooks or through a precision attachment made up of two coulisses (or guides) with a male-female connection, one of which is welded to a crown cemented on the pillar tooth and the other incorporated in the prosthesis.

Numerous types of precision attachments for partial removable prostheses are known, but all the types known at present have some drawbacks. In fact, some of these known precision attachments lack completely the possibility to adjust the retaining force between the male coulisse and female coulisse which is necessary for the stabilization of the prosthesis. Other known attachments having this characteristic require repeated and difficult operations for disassembling the various components of the attachment or for acting repeatedly upon very small screws or keys that are not easy to reach. In addition, none of the known attachments for removable prostheses are adjustable so that their working characteristics can be changed. They do not permit transformation of a rigid attachment into a semi-rigid attachment or into a cushioned (or dampened) attachment as is very often necessary, instead, after a weakening or lost of one of the pillar teeth.

SUMMARY OF THE INVENTION

The main object of the present invention is to overcome the above mentioned drawbacks.

The invention, as it is characterized by the claims, solves the problem by providing a precision attachment for a partial removable dental prosthesis which is easily made and has changeable working conditions.

With the use of an attachment of this type there are obtained the following results: the activation capacity, that is, the retaining force, is adjustable from a point of the alveolar saddle of the prosthesis through the rotation of a member about its own axis which is inclined to the direction of translation of the retention element of the coulisse incorporated in the prosthesis, and the working conditions can be varied by merely changing the conformation of the retaining small head which is to be inserted into the coulisse that is welded to the pillar tooth and, thereby, without changing the general arrangement of the prosthesis.

The advantages obtained through the present invention consist, essentially, in that it is possible to adjust the anchorage held by acting on the head of a screw surfacing on the alveolar saddle of the prosthesis; that said adjustment is obtained without disassembling the parts making up the attachment coulisse incorporated in the prosthesis; that the parts making up the coulisse incorporated in the prosthesis are kept in mutual arrangement without any blocking connections; that the sheath holding the components of the coulisse incorporated in the prosthesis is replaceable after possible wear due to galvanic erosion; that the retaining small head is an interchangeale element whose shape is in relation to the desired working characteristics of the attachment; that the small head may be removed from the male element while remaining connected with the female element of the attachment; and that an attachment realized according to the invention is of simple construction, easy application and safe working even after a long duty period.

BRIEF DESCRIPTION OF THE DRAWINGS

The invention will now be illustrated in more detail with the aid of the drawings which show one constructive embodiment.

FIG. 1 is an ensemble view of a partial prosthesis with removable attachment realized according to the invention, as it is applied in use;

FIGS. 2A, 2B and 2C are views of enlarged exploded axonometry, the three components making up the male element for the attachment of FIG. 1;

FIG. 3 is an enlarged axonometric view of a female element for the attachment of FIG. 1;

DESCRIPTION OF THE PREFERRED EMBODIMENTS

The attachments for a removable prosthesis illustrated in the Figures is made up of a first coulisse element intended to be incorporated in the prosthesis P and of a second coulisse element intended to be secured, in a traditional manner, to a pillar tooth D. The element to be incorporated in the prosthesis is shown in FIGS. 2A to 2C and comprises essentially:

a headstock 2 for connection to the female element of the attachment;

a box 3 for the adjustment of and retaining force;

a container 1 for holding headstock 2 and box 3.

Figure 4:
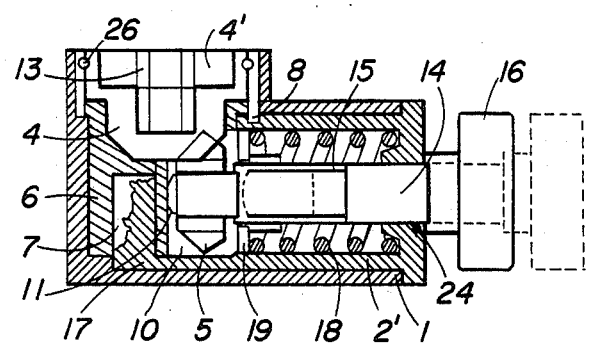
FIG. 4 is a vertical sectional view of the components of FIGS. 2A, 2B and 2C after their assembly, for a rigid attachment.

More particularly, the headstock 2 comprises a box-like sheath 2' shown in FIG. 4 which is open in correspondence with one of the vertical end walls and with a central hole 24 in correspondence with the other vertical end wall, which sheath can be fitted with accuracy into the horizontal wing or opening of the container 1 and is provided with a rise 17 and a slot 21; (FIG. 2C). A axial pivot 14 with thread 15 goes through the hole 24, and has a retaining small head integral therewith, while at the opposite end it projects with a square-section portion 10 and has a tapered tip 11 for the mounting of a bevel gear 5. On the threaded portion 15 of the pivot 14, a square plate 19 is screwed with the interposition of a spring 18.

The box 3 includes a body 6 with two longitudinal slides 9 (FIG. 2A), a transverse relief 8 intended to be housed in the corresponding slot 21 of the headstock 2, and with a cavity 7 (FIG. 4) for housing the corresponding relief 17 of the headstock 2. The body 6 is also suitably hollowed out to hold a cylindrical body 4' being provided at the bottom with a bevel gear 4 intended to mesh with the bevel gear 5. The body 4' is also provided with a groove 12 for driving the rotation of the pivot 4 and with an inner thread 13 for facilitating the withdrawl of the box 3 from the container 1. The square cross-sectioned part of container 1 which receives headstock 2 has a dimension A to B which is long enough to allow relief 8 of box 3 to engage slot 21 of headstock 2.

The container 1 is a box-like body having square cross section and developing at right angle, which is opened both in the horizontal upper part and in the vertical side end and has two vertical slots 20 to accomodate the corresponding guides 9 of the box 3.

As for the retaining small head and the sheath head of headstock 2, it is necessary, beforehand, to establish the function that the attachment has to perform.

In case of a rigid attachment, the small head 16 will be cylindrical with a flat base and the sheath head will be flat as shown in FIG. 4 of the accompanying drawings, so that the small head will be fitted into the throat of the female coulisse 51 (FIG. 3) of the attachment without any possibility to move.

Figure 5:
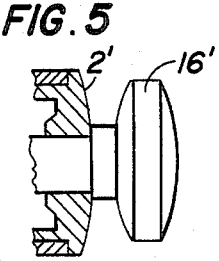
FIG. 5 is a detail view of a retaining small head for a semi-rigid attachment.

In case of a semi-rigid attachment, the small head 16' will be cylindrical with slightly convex bases and the head 2' of the sheath 2 will be slightly convex as shown in FIG. 5 of the accompanying drawings, so that the small head will be fitted into the female coulisse of the attachment with a limited possibility to rotate.

Figure 6:
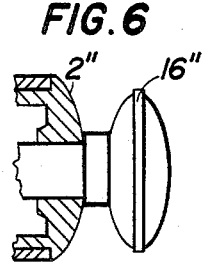
FIG. 6 is a detail view of a retaining small head for a sprung attachment.

In case of a cushioned, that is, hinge-like attachment, with vertical and horizontal rotation, the small head 16" will be cylindrical, with markedly convex bases, and the head 2" of the sheath 2 will be markedly convex as shown in FIG. 6 of the accompanying drawings, so that the small head will be fitted into the throat of the female coulisse of the attachment with a good degree of freedom for rotation.

Figure 7:
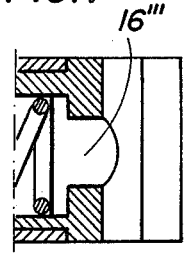
FIG. 7 is a detail view of a retaining small head shaped as a push-button.

In addition, the retaining small head 16 with the relevant pivot 14 may be replaced with a push-button 16''' as shown in FIG. 7 of the accompanying drawings.

Figure 8:
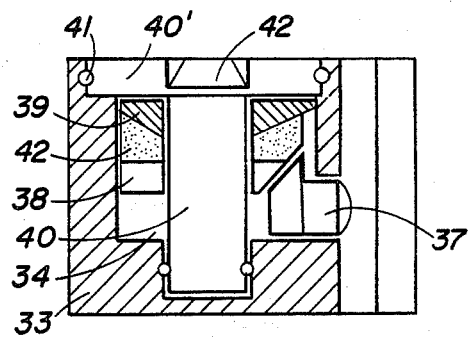
FIG. 8 is a vertical sectional view of the components making up the female element, for a simplified attachment with a push-button, according to the invention.

In the particular case in which the retention-activated device is in the form of a push-button, it is possible, according to the invention and as shown in FIG. 8 of the accompanying drawings, to reduce the coulisse of the attachment to be inserted into the prosthesis to a sheath 33 with a cylindrical cavity 34 opened on top and with a side hole for the head of the push button 37. The push button 37 has a side—downwardly inclined to the left—with which a plate 38 is in contact, said plate having a tapered and specular surface upon which a ring nut 39 acts. The ring nut 39 is screwed on the pivot 40 of the cylindrical body 40' and with the interposition of a pad (or bearing) 142 made of elastic material. The body 40' and the pivot 40 are suitably engaged with the base 30 through means known per se, such as, for example, elastic rings 41. The body 40' is further provided with a dovetail groove 42 for driving its rotation and drawing it out from the base 30.

In a simplified embodiment, in place of the pivot 40 with ring nut 39, the pad 142 and plate 38 shown in FIG. 8 of the accompanying drawings, a spring 44 acting by its lower part on an inclined pawl of the push-button 36, and a body 40' engaged with the base 30 through a thread (FIG. 9) may be provided.

Figure 9:
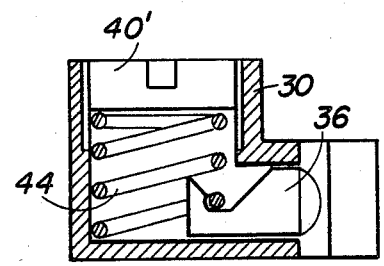
FIG. 9 is a vertical sectional view of the components making up the female element, for another simplified attachment with push-button, according to the invention.
Figure 10:
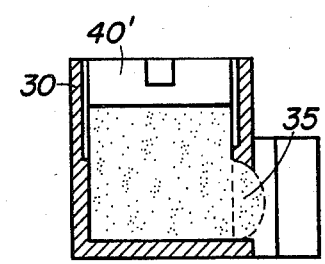
FIG. 10 is a vertical sectional view of the female element for a further simplified attachment with push-button.

In a further modified embodiment shown in FIG. 10, a block 35 made of elastic material incorporating the push-button is provided in place of the spring 44 and push-button 36 of the attachment of FIG. 9.

While specific embodiments of the invention have been shown and described in detail to illustrate the application of the principles of the invention, it will be understood that the invention may be embodied otherwise without departing from such principles.

I claim:

1. An attachment for a partial removable dental prosthesis comprising, a first coulisse for incorporation into the prosthesis, a second coulisse to be fixed to a pillar tooth, a cylindrical body mounted for movement to said first coulisse with respect to a first axis, a retention element mounted for movement to said first coulisse with respect to a second axis lying at an angle to said first axis, and interposed means operatively connecting said retention element to said cylindrical body so that movement of said cylindrical body with respect to said first axis causes movement of said retention element with respect to said second axis, said retention element having a head for frictional engagement with said second coulisse, said interposed means applying a resilient force against said retention element for continuously and adjustably changing the frictional engagement of said head against said coulisse with movement of said cylindrical body along said first axis.

2. An attachment according to claim 1, wherein said first axis is at right angles to said second axis.

3. An attachment according to claim 1, wherein said second coulisse has a rectangular opening, said head of said retention element being cylindrical with flat bases for engaging in said rectangular opening of said second coulisse for retaining said head without movement in said second coulisse.

4. An attachment according to claim 1, wherein said second coulisse has a rectangular opening, said head of said retention element being cylindrical and having convex bases for engagement in said rectangular opening of said second coulisse for permitting relative rotation between said first and second coulisses.

5. An attachment according to claim 1, wherein said first coulisse comprises a sheath having a threaded opening, said cylindrical body being threaded into said threaded opening of said sheath and being rotatable about said first axis, said retention element comprising an elastic body in said sheath beneath said cylindrical body with a portion extending outwardly from said sheath to form said head in the form of a push button.

6. An attachment according to claim 1, wherein said first coulisse comprises a sheath having a threaded opening, said cylindrical body being externally threaded and being threaded into said threaded opening of said sheath for rotation about said first axis, a spring disposed in said sheath and engaged against said cylindrical body, said head of said retention element being in the form of a pushbutton having an inclined shape engaged with said spring for pushing said pushbutton with movement of said cylindrical body along said first axis.

7. An attachment for a partial removable dental prosthesis comprising, a first coulisse for incorporation into the prosthesis, a second coulisse to be fixed to a pillar tooth, a cylindrical body mounted for movement to said first coulisse with respect to a first axis, a retention element mounted for movement to said first coulisse with respect to a second axis lying at an angle to said first axis, and interposed means operatively connecting said retention element to said cylindrical body so that movement of said cylindrical body with respect to said first axis causes movement of said retention element with respect to said second axis, said retention element having a head for frictional engagement with said second coulisse, said interposed means comprising a bevel gear connected to said cylindrical body, said cylindrical body being rotatably mounted to said first coulisse about said first axis, a box for rotatably receiving said cylindrical body and being mounted in said first coulisse, said box defining an upper base surfacing for an alveolar saddle of the prosthesis, said cylindrical body having a groove therein.

8. An attachment for a partial removable dental prosthesis comprising, a first coulisse for incorporation into the prosthesis, a second coulisse to be fixed to a pillar tooth, a cylindrical body mounted for movement to said first coulisse with respect to a first axis, a retention element mounted for movement to said first coulisse with respect to a second axis lying at an angle to said first axis, and interposed means operatively connecting said retention element to said cylindrical body so that movement of said cylindrical body with respect to said first axis causes movement of said retention element with respect to said second axis, said retention element having a head for frictional engagement with said second coulisse, said head of said retention element being cylindrical, said retention element including a threaded pivot fixed to said head, a bevel gear connected to said threaded pivot, an intermediate plate held in said first coulisse against rotation and into which said threaded pivot is threaded for movement of said retention element along said second axis with rotation of said threaded pivot, said cylindrical body being rotatably mounted to said first coulisse and having a further bevel gear mesh with said bevel gear of said retention element.

9. An attachment according to claim 8, including a box in said first coulisse for rotatably receiving said cylindrical body, a sheath in said first coulisse for rotatably receiving said threaded pivot, said first coulisse comprising a box-like container having square cross-sectioned parts extending at right angles to each other, said first axis being at right angles to said second axis, and said sheath and box being engaged respectively in said parts of said box-like container.

10. An attachment for a partial removable dental prosthesis comprising, a first coulisse for incorporation into the prosthesis, a second coulisse to be fixed to a pillar tooth, a cylindrical body mounted for movement to said first coulisse with respect to a first axis, a retention element mounted for movement to said first coulisse with respect to a second axis lying at an angle to said first axis, and interposed means operatively connecting said retention element to said cylindrical body so that movement of said cylindrical body with respect to said first axis causes movement of said retention element with respect to said second axis, said retention element having a head for frictional engagement with said second coulisse, said cylindrical body being mounted for rotation to said first coulisse, said cylindrical body having a threaded pivot, a ring nut mounted in said first coulisse having a threaded opening for receiving said threaded pivot of said cylindrical body, said head of said retention element comprising a pushbutton for movement along said second axis, said cylindrical body being rotatable about said first axis, said retention element including an inclined surface, an annular block engaged with said inclined surface and movable along said first axis with movement of said pushbutton along said second surface, and an elastic ring engaged between said annular block and said cylindrical body.

* * * * *

UNITED STATES PATENT AND TRADEMARK OFFICE
CERTIFICATE OF CORRECTION

PATENT NO. : 4,698,020

DATED : October 6, 1987

INVENTOR(S) : Ivano Menicagli

It is certified that error appears in the above-identified patent and that said Letters Patent is hereby corrected as shown below:

On the title page, Item [76], "Ivano Menicacci" should read

-- Ivano Menicagli --.

FIGS. 2A, 4, 7 and 9 should appear as shown on the attached sheet.

Signed and Sealed this

Twenty-fourth Day of May, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,698,020

DATED : October 6, 1987

INVENTOR(S) : Ivano Menicagli

It is certified that error appears in the above-identified patent and that said Letters Patent is hereby corrected as shown below:

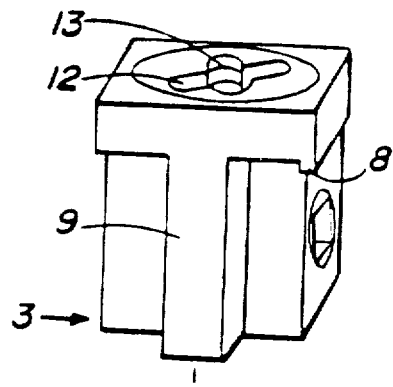

FIG. 2A

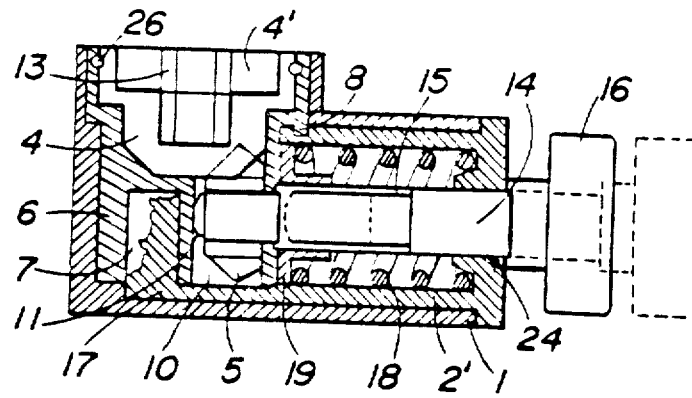

FIG. 4

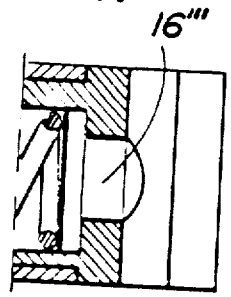

FIG. 7

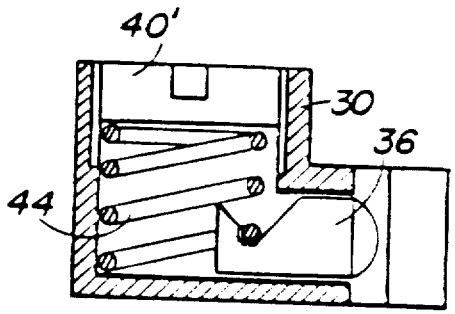

FIG. 9